(12) United States Patent
Greter et al.

(10) Patent No.: US 8,944,107 B2
(45) Date of Patent: Feb. 3, 2015

(54) DEVICE FOR OPENING A CLOSED FLUID CONTAINER

(75) Inventors: Andy Greter, Baar (CH); William Brem, Muri (CH); Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 1053 days.

(21) Appl. No.: 13/054,625

(22) PCT Filed: Jul. 14, 2009

(86) PCT No.: PCT/CH2009/000251
§ 371 (c)(1),
(2), (4) Date: Jan. 18, 2011

(87) PCT Pub. No.: WO2010/012114
PCT Pub. Date: Feb. 4, 2010

(65) Prior Publication Data
US 2011/0114212 A1    May 19, 2011

(30) Foreign Application Priority Data

Jul. 29, 2008  (CH) ........................... 1186/08
Jan. 21, 2009  (CH) ........................... 0089/09

(51) Int. Cl.
*A61C 5/06* (2006.01)
*B67B 7/92* (2006.01)
(Continued)

(52) U.S. Cl.
CPC ............... *B67B 7/92* (2013.01); *A61B 17/8805* (2013.01); *B01F 11/0054* (2013.01); *B01F 15/0215* (2013.01); *B01F 15/0223* (2013.01); *B01F 15/0226* (2013.01)

USPC .......... 137/896; 222/83.5; 222/87; 366/182.3

(58) Field of Classification Search
CPC ............. B01F 11/0054; B01F 15/0215; B01F 15/0226; B01F 15/0223; A61B 17/8805; B67B 7/92
USPC ........ 222/83, 87, 170; 366/139, 182.3, 182.4, 366/184, 189; 606/92, 93; 206/219
See application file for complete search history.

(56) References Cited

U.S. PATENT DOCUMENTS 3,506,006 A * 4/1970 Lange, Jr. ..................... 604/190
3,892,237 A * 7/1975 Steiner .......................... 604/200
(Continued)

FOREIGN PATENT DOCUMENTS

DE         29 21 565 A1    12/1980
DE         195 32 015 A1    3/1997
(Continued)

*Primary Examiner* — Yogendra Gupta
*Assistant Examiner* — Emmanuel S Luk
(74) *Attorney, Agent, or Firm* — Sughrue Mion, PLLC

(57) ABSTRACT

An opening device for opening a closed fluid container comprises a housing having a first chamber (1) for receiving the fluid container (3) and a second chamber (2) having an outlet (13). A part (6) of the fluid container that can be separated is arranged in the second chamber. A rotary drum (8) is rotatably supported in the second chamber. Said drum can be rotated from a starting position into a separating position in which it separates the separable container part from the fluid container. The rotational axis of the rotary drum is disposed at an angle to the connecting axis between the first and second chambers. A system for mixing at least two components uses such an opening device and a mixing container (18) having a connecting piece (19), to which the opening device is removably connected to establish a fluid connection.

16 Claims, 11 Drawing Sheets

(51) Int. Cl.
*A61B 17/88* (2006.01)
*B01F 11/00* (2006.01)
*B01F 15/02* (2006.01)

(56) References Cited

U.S. PATENT DOCUMENTS

| | | | |
|---|---|---|---|
| 4,779,763 A | 10/1988 | Klawitter | |
| 5,328,664 A * | 7/1994 | Ponsy | 422/84 |
| 5,555,007 A * | 9/1996 | Ceschin et al. | 347/87 |
| 5,628,353 A * | 5/1997 | Ruther | 141/330 |
| 6,296,149 B1 | 10/2001 | Long | |
| 6,312,149 B1 * | 11/2001 | Sjovall et al. | 366/130 |
| 6,364,103 B1 * | 4/2002 | Sergio et al. | 206/222 |
| 6,435,705 B1 * | 8/2002 | Long | 366/139 |
| 7,073,936 B1 * | 7/2006 | Jonsson | 366/139 |
| 7,112,205 B2 * | 9/2006 | Carrison | 606/92 |
| 8,132,959 B2 * | 3/2012 | Smit | 366/182.3 |
| 8,464,910 B2 * | 6/2013 | Larson et al. | 222/129 |
| 8,662,736 B2 * | 3/2014 | Vogt et al. | 366/139 |
| 2003/0155381 A1 * | 8/2003 | Chan | 222/394 |
| 2005/0070915 A1 * | 3/2005 | Mazzuca et al. | 606/93 |
| 2005/0105385 A1 * | 5/2005 | McGill et al. | 366/139 |
| 2005/0228396 A1 * | 10/2005 | Jonsson | 606/92 |
| 2006/0074433 A1 * | 4/2006 | McGill et al. | 606/92 |
| 2009/0057168 A1 * | 3/2009 | Smit | 206/221 |
| 2009/0171361 A1 * | 7/2009 | Melsheimer et al. | 606/93 |
| 2010/0091606 A1 * | 4/2010 | Kwan et al. | 366/139 |
| 2010/0301089 A1 * | 12/2010 | Muller | 225/103 |
| 2012/0006874 A1 * | 1/2012 | Vogt et al. | 225/103 |
| 2013/0135959 A1 * | 5/2013 | Vogt et al. | 366/139 |

FOREIGN PATENT DOCUMENTS

| | | |
|---|---|---|
| DE | 198 41 722 A1 | 3/2000 |
| EP | 0 079 983 A1 | 6/1983 |
| EP | 0 972 499 A2 | 1/2000 |
| WO | 97/07748 A1 | 3/1997 |

* cited by examiner

DEVICE FOR OPENING A CLOSED FLUID CONTAINER

TECHNICAL FIELD

The present invention relates to a device for opening a closed fluid container and to a system for mixing at least two components. In particular, the present invention relates to a device for opening an ampule with a separable ampule part, and to a system for mixing at least two components, of which at least one of the components is stored in such an ampule.

PRIOR ART

In various fields of medicine and technology, it is necessary that substances for treatment or for processing are mixed just shortly before their use, for example because the finished mixture is unstable or, for example, because it is advantageous to handle it in separate components until the time of use. In the medical field, for example, this is known in the processing of bone cement, for example in bone reconstructions, or in the fitting of implants such as hip joints or for intervertebral disk reconstructions. Such substances are also used, for example, in the treatment of tissue or wounds or for stopping bleeding. For example, glues for wounds are mixed from two or more components shortly before use. Other applications that require such a mixing technique are found in the field of pharmacy, since many medicines can be mixed only shortly before they are used.

In the production of bone cement (PMMA), for example, a fluid monomer, generally MMA (monomeric methyl methacrylate) is mixed with a powdery component. The fluid is generally provided in an elongate glass ampule having, at one end, a head area that can be separated from the ampule by a slight impact or a bending force. In most cases, a predetermined break point is provided on this separable part. The powdery component is provided in another container, which can sometimes also serve as a mixing container. Shortly before the bone cement is applied, the ampule containing the fluid monomer is broken open and the fluid is added to the dry component and mixed with the latter. When the ampule is broken open, there is a risk of injury on the broken edges, and there is the danger of splintered material getting into the fluid. Moreover, personnel are exposed to the aggressive vapors.

In the prior art, several devices are known that make it easier to break open a container containing a fluid and to mix the fluid with another component. For example, U.S. Pat. No. 6,296,149 discloses a device in which the head of an ampule is separated by a rotary device. Arranged in the rotary device are several separating elements which, upon rotation, can strike against the head of an ampule and separate said head. The ampule is held in a housing, and the rotary device turns relative to the housing. The rotation axis about which the rotary device is turned is parallel and offset in relation to the ampule axis. The rotary device must therefore be constructed extending well beyond the ampule housing, with the result that the overall unit made up of ampule housing and rotary device has a long projecting configuration. To turn the rotary device, the ampule housing has to be gripped in one hand and the rotary device in the other hand. In order to separate the ampule head, a force is applied exclusively via the relative rotation movement of these two parts and has to act against the frictional forces of the rotary device and the opposing force of the ampule head. Consequently, a great deal of force has to be applied to separate the ampule head.

EP 0 972 499 discloses a device for breaking open an ampule, in which device a base element is provided for receiving the ampule, and a cap element that can be screwed onto the base element. The cap has a breaking structure which, when the base element and the cap are screwed together, breaks open a bottom of the ampule. In this device for breaking open the ampule, two elements are turned relative to each other along a single rotation axis. Also in this device, the ampule is broken open by a purely rotational force when the structural elements are turned together. There is also a danger of the broken open part of the ampule dropping into the interior of the ampule and thus contaminating the fluid by splinters and the like.

WO 97/07748 discloses a device for mixing and dispensing a product made up of two components. One of the two components is a powder and is located, together with a mixing element and dispensing elements, in a chamber. The other component is liquid and is stored in an ampule. The ampule is received in a housing that is pivotable relative to the chamber about a pivot axis extending transversely with respect to the longitudinal axis of the ampule. The ampule head is held stationary with respect to the chamber in a bearing element and is broken off from the ampule body by the pivoting movement. The second component thus emerging from the ampule is transferred laterally in the direction of the pivot axis out of the housing into the chamber containing the first component. For this purpose, a relatively complicated arrangement of channels is present between housing and chamber.

This device is relatively awkward to handle, and emptying not just of the ampule body, but also of the ampule head, is ensured only if the whole device is held in a suitable orientation in which the ampule head points upward. The arrangement of channels for transferring the second component into the chamber with the first component is also very complicated and is therefore expensive to produce and susceptible to failure. There is no provision, nor is it possible without further structural modifications, for the device for breaking the ampule to be designed separately from the mixing and dispensing device, and instead these devices form an inseparable unit.

DISCLOSURE OF THE INVENTION

It is an object of the present invention to make available a device for opening a closed fluid container, specifically a device that can in principle be designed independently of a mixing and dispensing device, is easy to operate and permits safe handling of the mixing components used. It is also desirable that little force is needed to open the fluid container, that the device has a space-saving design and in particular permits advantageous utilization of the forces applied. It is also an object of the present invention to make available a system for mixing at least two components, which system allows the components to be brought together with only a few maneuvers and is safe and hygienic to handle.

According to the present invention, these objects are achieved by a device according to claim 1 for opening a closed fluid container and by a system according to claim 12 for mixing at least two components.

An opening device for opening a closed fluid container according to the invention comprises:
- a housing with a first chamber for receiving the fluid container and with a second chamber connected to the first chamber and open toward the first chamber and having an outlet, the second chamber being designed to receive a separable part of the fluid container, and
- a rotary drum disposed in the second chamber rotatably about a rotation axis and having at least one separating element which, in a starting position, is offset in relation to the separable container part and, by a rotation of the rotary drum about the rotation axis, is adapted to be brought to a separating position, in which it separates the separable container part from the fluid container, the first and second chambers defining a connection axis, and the rotation axis of the rotary drum extending at an angle to this connection axis, the second chamber being shaped like a drum and having a jacket wall that extends about the rotation axis of the rotary drum, and the outlet of the second chamber being formed in the jacket wall of the second chamber.

A separable part of the fluid container thus protrudes from the first chamber into the second chamber. Chambers are also to be understood merely as different areas of the housing, the separable part of the fluid container coming to lie in one area and the rest of the container coming to lie in another area. Moreover, the opening device comprises at least one separating element which is mounted rotatably or pivotably in the second chamber and which is arranged offset in relation to the separable container part in a starting position and is rotatable or pivotable to a separating position in which it separates the separable container part from the fluid container. The rotation axis of the rotary drum is arranged at an angle to a connection axis between the first and second chambers of the housing or equivalently to the axis of the fluid container. This permits very simple handling. The outlet is arranged in the jacket wall of the second chamber. This makes it very easy to remove the fluid from the second chamber. In addition, it is thus possible to provide a connecting piece at the outlet, via which connecting piece the opening device can easily be connected in a releasable manner to another part, e.g. a mixing and dispensing device.

The housing preferably has an elongate design. The first chamber can be sleeve-shaped. The second chamber is drum-shaped and adjoins the first chamber, the chambers being juxtaposed in such a way that a connection axis is obtained in the direction of juxtaposition. The two axes of the two chambers are arranged at an angle to each other, preferably perpendicular to each other. The fluid container can be provided as a conventional ampule made of glass or plastic. The separable container part is preferably provided as a kind of ampule head with a predetermined break point in order to facilitate separation of the ampule head. The fluid container can be inserted into the first chamber of the housing until the separable container part protrudes into the second chamber. By means of limit stops inside the housing, the fluid container is prevented from being advanced farther into the housing. At the place of insertion for the fluid container, the housing can be closed by a closure piece in such a way that the fluid container is held securely in the first chamber. For this purpose, the closure piece can, for example, have a flexible pressure element, for instance a rubber piece, which presses on the rear part of the ampule. The housing can also be used to store and transport the fluid container.

In the second housing chamber, in a starting position, the at least one separating element is arranged offset in relation to the separable part of the fluid container. The offset position of the separating element can, for example, entail the separating element being arranged next to or also under the separable part of the fluid container. The important point is that the separating element is offset in relation to the rotation axis of the separating element in such a way that it is movable by a rotation of the rotary drum, preferably movable on a circular path. Since the rotation axis of the rotary drum extends at an angle to the axis of the fluid container, or equivalently to the connection axis between the first and second chambers of the housing, the separating element is moved toward the separable part of the fluid container upon rotation of the rotary drum. As soon as the separating element hits the separable container part, forces act on the separable part, said forces attacking the latter from the side and thereby separating the separable part of the fluid container from the part of the fluid container held securely in the first chamber. The pressure force or shearing force acting on the separable part from the side is sufficient to separate said part, if appropriate at a predetermined break point. However, it is also possible in principle for the at least one separating element to have a separating edge or even a cutting edge which, during a rotation, strike the separable part and break or separate the latter. It is also conceivable that the separating element can be moved beyond the separating position. However, a guide is preferably provided that limits the rotation movement between the two positions.

The axis of the fluid container is understood as the axis along which the greater part of the fluid container and the adjoining separable part of the fluid container are arranged. In the case of a sleeve-shaped first housing chamber in which an ampule is fitted, this axis corresponds to the axis of the housing chamber or the axis of the ampule.

The rotation axis of the rotary drum is arranged at an angle to the connection axis between the first and second chambers or, equivalently, to the axis of the fluid container. The angle between the axes is preferably such that the rotary drum can be gripped at the side of the housing and turned manually. It is particularly preferable for the rotation axis of the rotary drum to be substantially perpendicular to the axis of the fluid container.

The device according to the invention for opening the fluid container can have a slim shape, since rotation of the rotary drum can take place substantially within the dimensions of the housing. No projecting additional elements are needed on the housing. The separating element is provided, in a way that saves space, near the separable part of the fluid container. By means of the angled arrangement of the axes, a lever action can be utilized. This lever action arises from the relative movement between the rotary drum and the elongate housing. If the housing is held in one hand at a distance from the rotary drum and the rotary drum is rotated using the other hand, the distance acts as a lever and makes the rotation movement easier.

The separating element preferably acts, or the separating elements preferably act, on the separable container part at least from one side of the container part, particularly preferably from two opposite sides of the container part. The separable container part can, for example, engage in an opening, a niche or a recess of an individual separating element or can protrude between two or more separate separating elements. Upon rotation of the separating element or of the separating elements, the shearing force acts on at least one side of the separable container part, preferably on two sides, such that the separation is made easier. The separating element is particularly preferably designed such that it securely holds the separable container part after the separation.

The rotary drum can be inserted almost with a form fit into the drum-shaped or sleeve-shaped second container chamber so as to bear substantially on the inner wall of the housing sleeve. The separating elements can be designed, for example, as pins or projections extending from the bottom of the rotary drum, in which case they are arranged offset from the center point of the drum. The rotary drum can have a handle which protrudes from the second container chamber and which is provided for turning the rotary drum in the chamber. The handle is preferably elongate in the manner of a grip plate extending from the rotary drum in order to allow simple turning. The handle can be configured asymmetrically in relation to the rotation axis and, for example, can protrude on one side beyond the circumferential wall of the rotary drum or the jacket wall of the second chamber, so as to make the rotation position of the rotary drum easier to discern and increase the lever action between housing and rotary drum. However, other configurations of the handle are also conceivable in principle, provided that they enable turning of the rotary drum.

The rotary drum is inserted into the housing chamber by means of, for example, a snap-fit connection and preferably cannot be removed therefrom. This eliminates any risk of injury caused by separated container parts. However, it is also conceivable for the rotary drum to be removable from the second container chamber, so as to permit easy disposal of a separated part of the fluid container.

The rotary drum has a first opening through which the separable part of the fluid container protrudes into the interior of the drum and which is provided along the circumference of the rotary drum. In its circumferential wall, the rotary drum can also have a passage which, in a starting position, is arranged offset in relation to the outlet of the second container chamber, such that the outlet of the second chamber is closed by the circumferential wall of the rotary drum. When the rotary drum is rotated to the separating position of the separating elements, the passage in the rotary drum comes to lie opposite the outlet of the second container chamber. A fluid connection is thus established between the interior of the rotary drum and the outlet from the second container chamber, such that the fluid can emerge from the opening device. The rotary drum thus assumes the function of a valve that opens or closes the outlet for the fluid from the housing.

In a preferred embodiment, the passage in the rotary drum has a filter. The filter can in particular hold back splinters or fragments that are produced when the part of the fluid container is separated. The filter can be integrated directly in the rotary drum or can be fitted as a separate structural part onto the rotary drum.

In another embodiment of the present invention, a guide is provided between the second container chamber and the rotary drum, said guide having two rotation limit stops, one for a first direction of rotation and one for a second direction of rotation. When the rotary drum is turned from the starting position to the separating position in a first direction of rotation, it is stopped on the first rotation limit stop of the guide. In this stopped position, or separating position, the separable part of the fluid container is separated from the fluid container and the passage in the rotary drum lies opposite the outlet of the housing. In this defined position, the fluid can emerge from the fluid container and out of the housing of the device. When the rotary drum is turned in the opposite direction of rotation, from the separating position to the starting position, the rotation is stopped by the second rotation limit stop of the guide. In this second stopped position, the circumferential wall of the rotary drum lies opposite the outlet of the second housing chamber, and escape of fluid from the housing is not possible. The valve is closed in this position.

The rotary drum can thus assume two functions at the same time. It serves, on the one hand, to open the fluid container, since the separable part of the fluid container is separated by rotation of the rotary drum, and, on the other hand, to regulate the flow of fluid out of the housing of the device.

In another embodiment, the housing can have a vacuum connector, so as to be able to generate an underpressure in the housing. The vacuum connector is advantageously regulated by the valve function of the rotary drum. Such an opening device with a vacuum connector can be used particularly advantageously in a system for mixing at least two components, as is explained in more detail below.

Moreover, the opening device can have an indicator that shows the separating position of the separating element. Such an indicator can, for example, be a color marking or line marking which is provided on the rotary drum and which is turned relative to a marking on the housing corresponding to a separating or starting position. However, the marking can also be provided by the handle which is arranged on the rotary drum and which, in a starting position, lies transverse to the longitudinal axis of the first housing chamber and thus indicates a closed valve and which, after being turned, lies in the longitudinal direction on the axis of the first housing chamber and thus indicates an opened valve and a separated part of the fluid container. Further configurations of an indicator are of course possible.

Moreover, in an advantageous embodiment of the invention, a connecting piece is provided at the outlet of the second chamber of the fluid container, via which connecting piece the housing can be connected to a further structural element, for example another container. Such a connecting piece can be provided, for example, as part of a threaded connection, of a Luer lock connection or of a bayonet connection.

According to a further aspect of the present invention, a system for mixing at least two components is provided which comprises at least one opening device as described above and a mixing container, to which the at least one opening device is connected permanently or removably to establish a fluid connection. There is therefore a fluid connection between the housing of the opening device and the interior of the mixing container. For this purpose, the mixing container can, for example, have a connecting piece which cooperates with the connecting piece on the outlet of the second housing chamber of the opening device. Accordingly, the opening device can, for example, be screwed onto the mixing container or fitted thereon by means of a bayonet connection. It is also possible to provide a closure mechanism, for example a membrane, which closes the opening of the mixing container prior to the attachment of the opening device and which is opened at the time of attachment.

In one embodiment, the system is provided for a first component in the form of a fluid in a fluid container and a second component in the form of a solid, the solid preferably already being accommodated in the mixing container. The solid can of course also be provided in an additional container and be introduced into the mixing container just before mixing. In principle, it is possible for further opening devices with further components to be connected to further connecting pieces on the mixing container. Moreover, conventional fluid containers or other containers can also be additionally connected to the mixing container.

The system is suitable for mixing any kind of multi-component mixtures. It can be used particularly advantageously for multi-component applications with aggressive or readily volatile substances that are stored in a glass ampule. One example of use is the mixing of bone cement, in which a monomer, for example MMA, is provided in the opening device according to the invention and the powdery cement substance is already stored in the mixing container. It is also possible, for example, to mix gels together using a system according to the present invention.

In one embodiment of the mixing system, the mixing container can have a mixing paddle or stirring paddle mounted movably in the mixing container in order to thoroughly mix the components inside the mixing container. The paddle for this purpose can be designed according to the viscosity of the mixture. The mixing procedure can take place before or after the opening device is removed from the mixing container. The mixing or stirring paddle can, for example, be provided on a piston rod which at one end protrudes from the mixing container and at the other end has a mixing device, for example in the form of a paddle. For delivery, the piston rod is preferably removed or broken off from the paddle, and a delivery mechanism, for example in the form of a pressure gun, is attached to the mixing chamber. Instead of the opening device, it is possible to attach to the connecting piece of the mixing container a nozzle, a snorkel or a needle serving as a dispensing device for the mixed product. Through this dispensing device, the mixed product can be dispensed from the mixing container by means of the delivery mechanism.

It is also possible that, in order to dispense the mixture, an additional surface element is provided on the paddle, which surface element then acts as a kind of piston inside the mixing container and, when moved forward, causes the mixture to be dispensed. Such a surface element can be arranged on the paddle, for example, if the latter is pressed by the piston rod against the surface element, which is already located in the interior of the mixing container, and the piston rod is then broken off.

In another embodiment of a mixing system according to the invention, a device is provided for generating an underpressure in the system. For example, the opening device can have a vacuum connector through which an underpressure can be generated in the interior of the system. The vacuum connector can have a nonreturn valve, so as to be able to maintain the generated underpressure in the system after a vacuum generator has been removed. With the vacuum connector, the housing of the opening device and therefore the interior of the rotary drum and of the mixing chamber can be provided with underpressure before the ampule head is separated. When the ampule opens, the fluid is therefore sucked out of the ampule, since there is by comparison a higher pressure in the ampule.

The vacuum connector is preferably provided on the housing chamber with the rotary drum. The generation of the underpressure is preferably controlled by the position of the rotary drum. If the circumferential wall of the rotary drum lies opposite an outlet from the housing or opposite the connector for generating the underpressure, it acts as a closed valve. However, if the rotary drum is turned to a position in which one of its openings lies opposite the housing outlet or the underpressure connector, it acts as an opened valve. The rotary drum therefore has a vacuum rotation position in which a vacuum is applied to the system. The rotary drum is turned from the starting position to the vacuum position in which the individual volumes of the housing and of the mixing container are interconnected. In this position, the valve is opened. An underpressure is then generated in the system, for example by means of a pump. The system can be separated from the pump, the underpressure being maintained by means of the nonreturn valve. The rotary drum is turned to the separating position, in which it separates the separable container part. The vacuum assists the emptying of the container or of the ampule. Moreover, an underpressure also prevails in the system during the mixing procedure, such that air inclusions in the mixture can be reduced or completely ruled out.

In principle, it is also conceivable that a connector for generating an underpressure in the system is provided on the mixing container. This is advantageous, for example, if there are no mixing components in the mixing container and several containers with mixing components are connected to the mixing container.

BRIEF DESCRIPTION OF THE DRAWINGS

Preferred embodiments of the invention are shown in the drawing, which is not to be interpreted in any way as limiting the invention. Features of the invention that appear from the figures in the drawing are to be understood as belonging to the disclosure. In the drawings.

DESCRIPTION OF PREFERRED EMBODIMENTS

Figure 1:
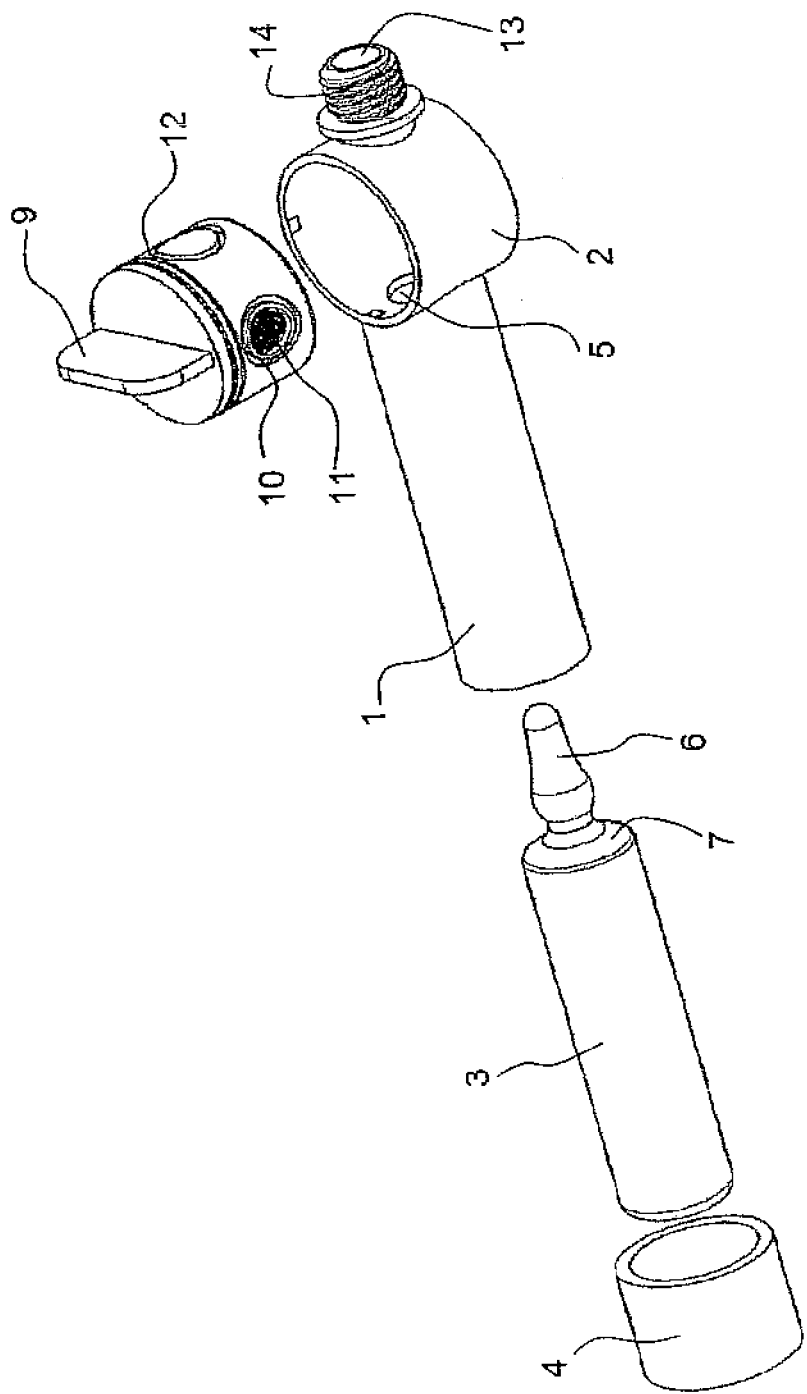
FIG. 1 shows an exploded view of a first embodiment of an opening device according to the invention.

In FIG. 1, a first embodiment of an opening device for opening a closed fluid container according to the present invention is shown with the individual structural elements in an exploded view. The opening device comprises a housing with a first housing chamber 1 and an adjoining second housing chamber 2. The first housing chamber 1 is sleeve-shaped and is suitable for receiving a fluid container in the form of a glass ampule 3. A closure cap 5 can be fitted onto one end of the first chamber 1. The other end of the chamber 1 is adjoined by the second housing chamber 2, which is likewise sleeve-shaped. The axes of the first housing chamber and of the second housing chamber are arranged at an angle of 90° to each other. An opening 5 is provided at the transition from the first housing chamber to the second housing chamber. The glass ampule 3, which has a separable head part 6, is inserted through the open end of the first housing chamber 1 into the first housing chamber 1 until the head part 6 protrudes through the opening 5 into the second housing chamber 2 and abuts with its shoulder 7 against the circumferential edge of the opening 5. The closure cap 5 is then fitted onto the opening of the first housing chamber 1, such that the ampule 3 is accommodated securely in the housing of the opening device.

A rotary drum 8 can be inserted into the second housing chamber 2. The rotary drum is likewise sleeve-shaped and is designed with an exact fit for the second housing chamber 2. The rotary drum 8 has a handle 9, which protrudes vertically in the form of a raised plate from a side surface of the rotary drum 8. A passage 10 is provided on the circumferential surface of the rotary drum 8, which passage 10 is provided with a filter 11. The passage 10 is arranged on the outer circumference in the line of continuation of the handle 9. A sealing ring 12 is provided annularly around the outer circumference of the rotary drum 8 and, when the rotary drum 8 is inserted into the second housing chamber 2, the sealing ring 12 seals off the space between the outer circumference of the rotary drum and the inner circumference of the second housing chamber.

At one end lying opposite the first housing chamber 1, the housing chamber 2 has an outlet 13 in its jacket wall (circumferential wall). This outlet opens into a connecting piece 14, which has a thread on its outer circumference.

In this embodiment, the connection axis between the first chamber 1 and the second chamber 2 of the housing corresponds substantially to the axis of the sleeve-shaped housing chamber 1, since the housing chamber 2 adjoins the first chamber in this direction. The rotary drum 8 can be inserted rotatably into the second housing chamber 2, such that the rotation axis of the rotary drum is substantially perpendicular to the connection axis of the housing chambers. It would also be conceivable to mount the annular second housing chamber on the first housing chamber in such a way that the axis of the rotary drum is arranged, for example, at an angle of between 60° and 90°.

Figure 2:
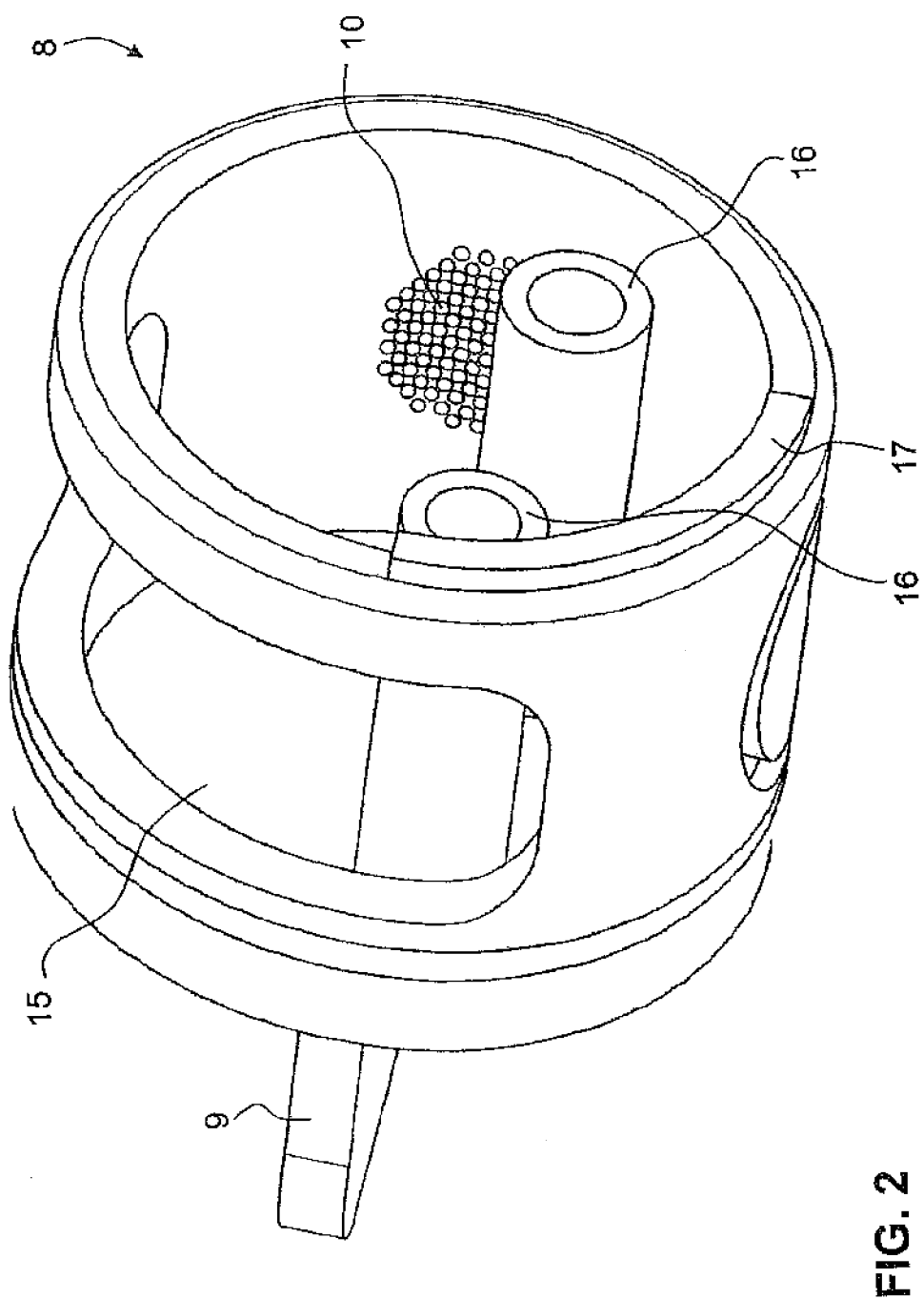
FIG. 2 shows a three-dimensional view of the rotary drum of the opening device from FIG. 1.

FIG. 2 shows a three-dimensional view of the rotary drum 8. The handle 9 can be seen on the left-hand side of the drawing, and the rotary drum is shown cut open on the right-hand side of the drawing. The passage 10 in the circumferential wall is shown in the form of a large number of small openings in the wall of the rotary drum. The filter 11 is formed by the fact that the diameter of the holes is small enough to hold back constituents that are to be filtered out. An elongate opening or oblong hole 15 is also present in the circumferential wall of the rotary drum 8 and extends in a sector of ca. 90° on the circumference of the rotary drum, and the size of the opening is such that the head part 6 of the ampule passes through the oblong hole and into the interior of the rotary drum 8. Two pins 16 protrude from an inner side surface of the rotary drum 8 and into the interior of the rotary drum. The pins 16 together form the separating element. According to the invention, however, it is in principle also possible for only one such pin 16 to be provided as separating element. The pins 16 are each offset in relation to the center point of the rotary drum 8 in such a way that, when the rotary drum is turned, they are turned or pivoted about the center point.

A guide edge 17 is provided on the side of the rotary drum that lies opposite the side with the handle and that comes to lie on a bottom surface of the housing chamber 2. A guide groove in which the guide edge 17 can engage is in turn provided on the bottom surface of the housing chamber 2. The guide groove is, for example, let into the bottom surface annularly about an angle of 180°. The guide edge 17 in turn extends about an area of 90° on the outer face of the rotary drum. This has the effect that the rotary drum is rotatable about 90° within the guide groove until it abuts against the respective ends of the guide groove.

Figure 3B:
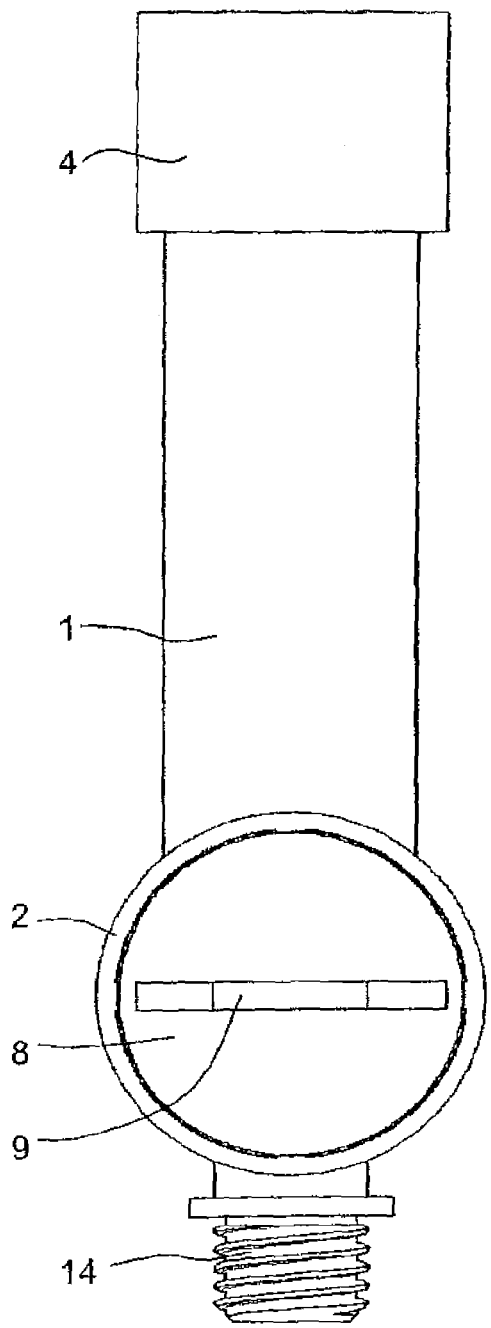
FIG. 3b shows a view according to FIG. 3a, seen from the outside.
Figure 3A:
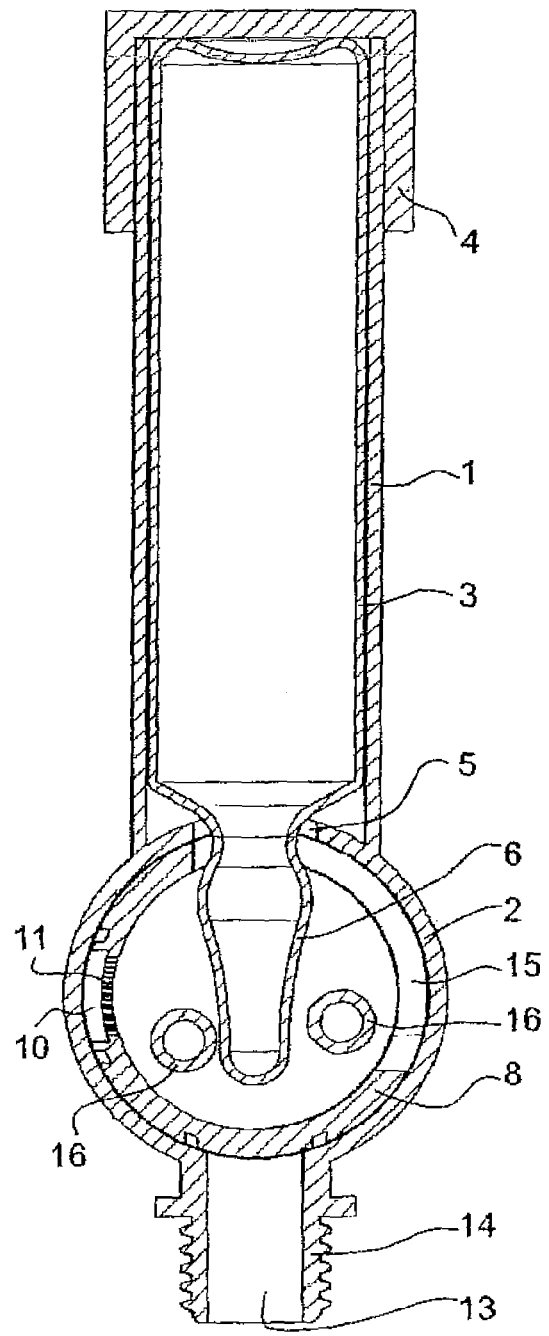
FIG. 3a shows a sectional view of the opening device from FIG. 1 in a starting position.

FIG. 3*a* shows a sectional view of the opening device in an assembled state. The ampule 3 is inserted into the first housing chamber 1, and the chamber is closed by the closure cap 4. The head part 6 of the ampule protrudes through the opening 5 into the second housing chamber 2 and into the interior of the rotary drum 8. The head part 6 of the ampule comes to lie between the two pins 16. The rotary drum 8 is shown in a starting position in FIG. 3*a*. The circumferential surface of the rotary drum 8 comes to lie opposite the outlet 13 and closes the latter. For its part, the passage 10 in the rotary drum 8 comes to lie opposite the inner circumferential surface (inner jacket surface) of the second housing chamber 2. The interior of the housing of the opening device is thus closed off from the outside in the starting position.

FIG. 3*b* shows the outside view of the sectional view from FIG. 3*a*. The handle 9 of the rotary drum 8 is oriented transversely with respect to the longitudinal axis of the ampule 3 in the interior of the housing.

This transverse position indicates that the passage 10 and the outlet 13 are not congruent and, consequently, the interior of the rotary drum 8 is closed off from the outside. The rotary drum 8 thus assumes a valve function for the through-flow of the fluid as soon as the latter emerges from the ampule, the valve being closed in this position.

Figure 4B:
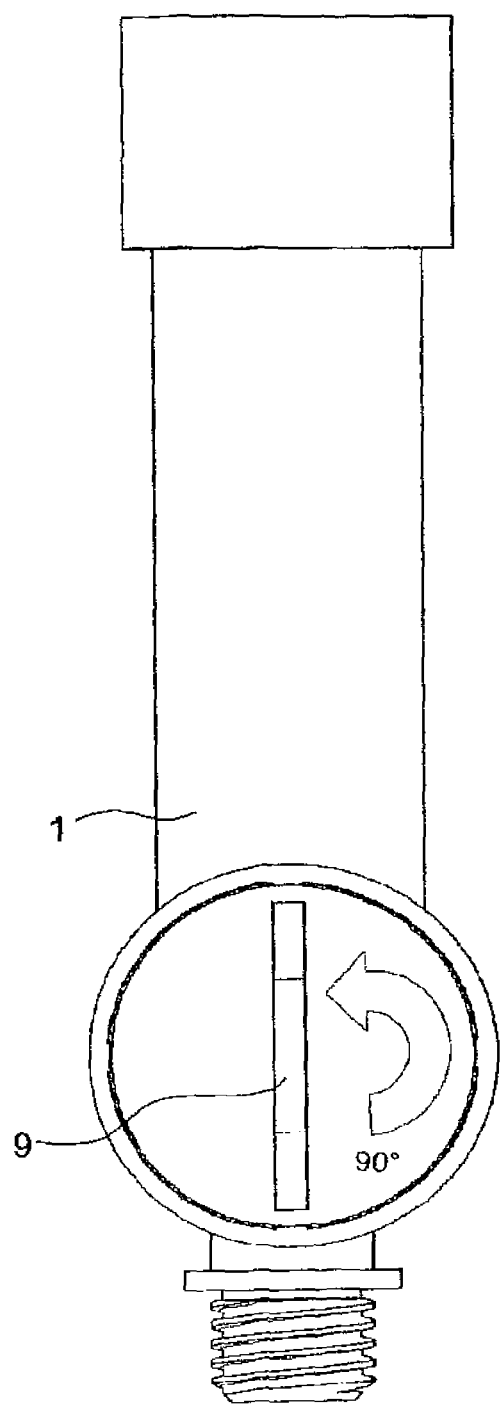
FIG. 4b shows a view according to FIG. 4a, seen from the outside.
Figure 4A:
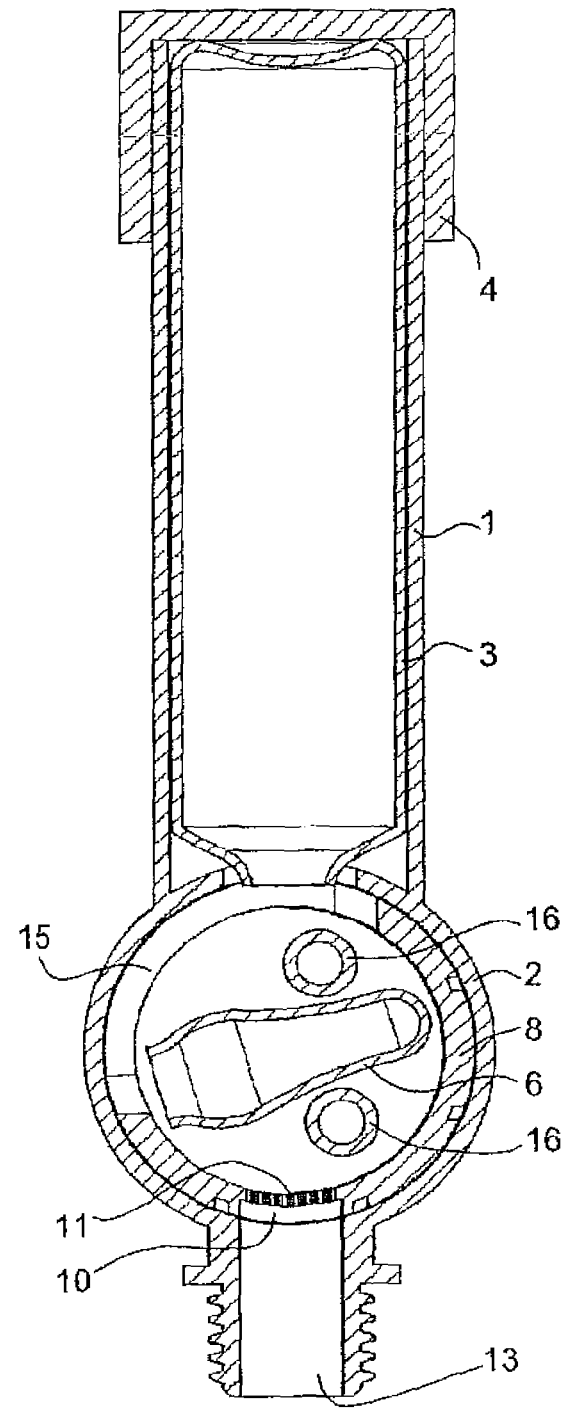
FIG. 4a shows a sectional view of the opening device from FIG. 1 in a separating position.

FIG. 4*a* shows the opening device in a separating position in which the separable head part 6 is separated from the glass ampule 3. For this purpose, the rotary drum 8 was turned through 90° inside the second housing chamber 2. The pins 16 are turned along with this and strike against the outside of the head part 6 of the glass ampule 3. A force is transmitted to the head part 6 and the head part breaks off from the ampule 3. The two pins 16 engage on opposite sides of the head part 6. The pins 16 are thus arranged tight on the outer surface of the head part 6, in such a way that the head part 6 is held by the two pins 16 after the ampule 3 has been broken off.

When the rotary drum 8 is rotated, the passage 10 with the filter 11 is at the same time made congruent with the outlet 13. In this way, a fluid connection is created between the interior of the rotary drum 8, the second housing chamber 2 and the outside of the housing.

Since the head part 6 of the glass ampule 3 has been broken off from the latter, the fluid can flow out of the interior of the ampule 3, through the oblong hole and into the interior of the rotary drum 8. From there, it can flow out of the housing through the filter 11, the passage 10 and the outlet 13. The broken-off head part 6 is held by the pins 16 in such a way that it does not block the passage 10 with the filter 11, and fluid possibly remaining in the head part can flow off from the head part.

FIG. 4*b* shows the outside view of the opening device from FIG. 4*a*. It will be seen that the handle 9 of the rotary drum 8 has been turned through 90° into the separating position. The handle 9 is therefore now oriented in the longitudinal direction of the axis of the glass ampule and thus indicates an open valve.

Figure 5B:
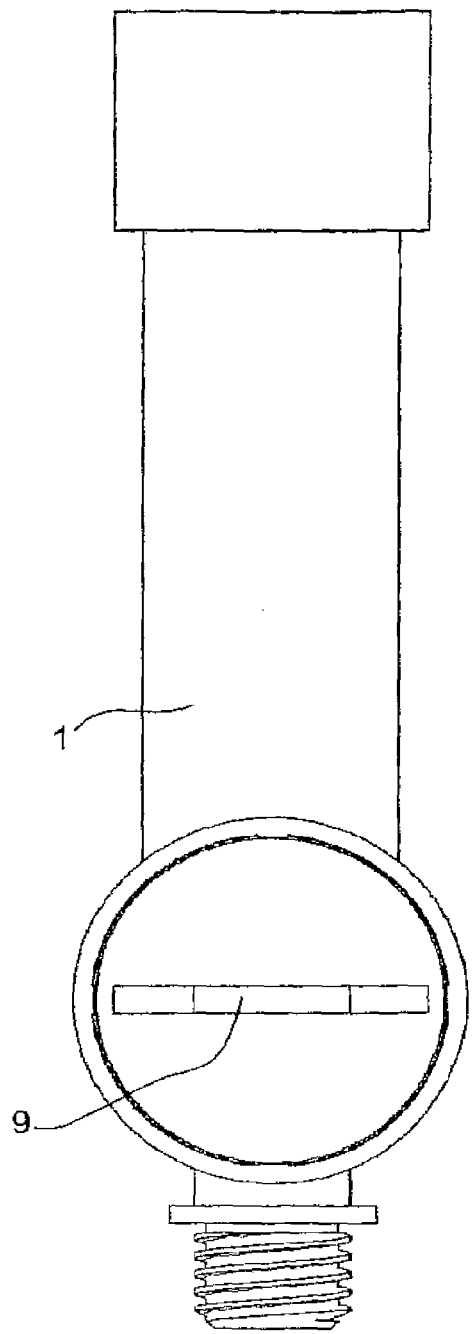
FIG. 5b shows a view according to FIG. 5a, seen from the outside.
Figure 5A:
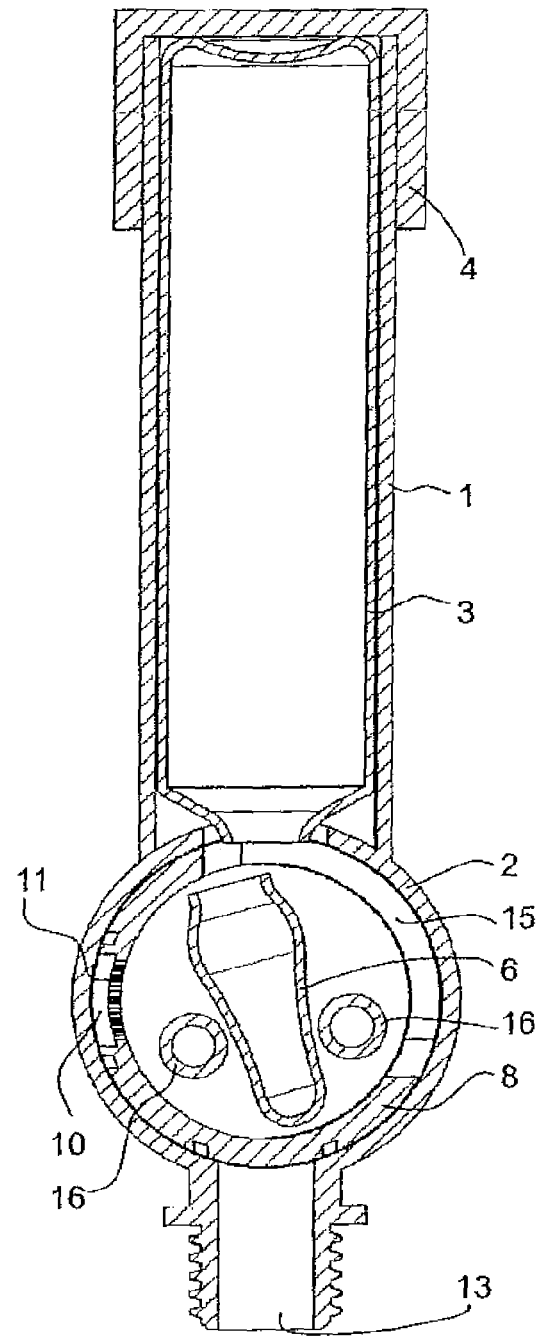
FIG. 5a shows a sectional view of the opening device from FIG. 1 after a part of the fluid container has been separated.

FIG. 5*a* shows the opening device in a closed position. In this position, the rotary drum 8 has been turned back again until the outer circumference of the rotary drum lies opposite the outlet 13 and the passage 10 with the filter 11 lies opposite the inner circumference of the housing chamber 2, such that the valve formed by the rotary drum 8 and by the second housing chamber 2 is closed. The head part 6 is still held by the pins 16. The valve function can be used, for example, to regulate the amount of a fluid that is intended to be discharged from the housing. It also prevents the mixing product from getting into the rotary drum. The opening device can be disposed of in this closed position. By using the opening device, it has been possible to dispense the content of the ampule safely and without any risk of injury caused by the breaking open of the ampule.

FIG. 5b shows the outside view of the opening device from FIG. 5a. It will be noted that the rotary drum 8 has again been turned through 90° inside the second housing chamber. The handle 9 is arranged transversely with respect to the longitudinal axis of the ampule and indicates a closed valve.

The turning of the rotary drum 8 from the starting position according to FIG. 3a to the separating position according to FIG. 4a is guided by the guide edge 17 and the associated guide groove in the housing chamber 2. By means of this guide, the rotary drum 8 can be rotated inside the housing chamber 2 by 90° in each case. Depending on the specific requirements of an application, the guide groove and the guide edge can also define other angle settings, for example 60° or 120°.

Figure 6:
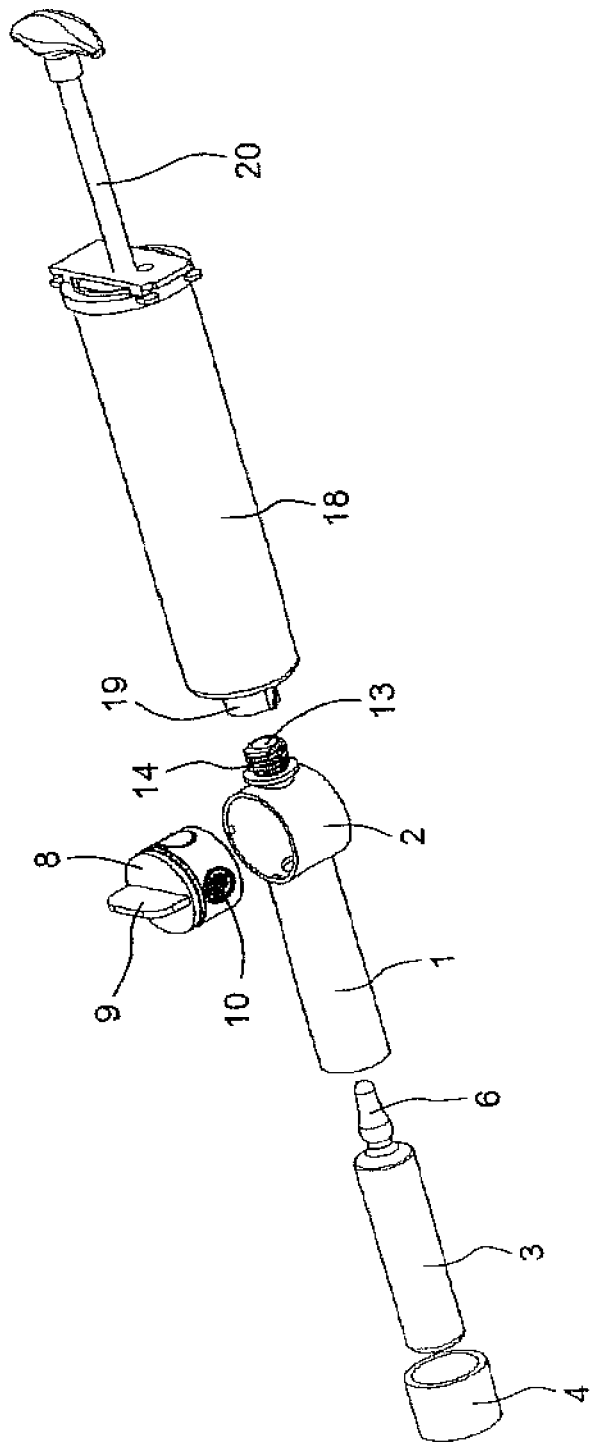
FIG. 6 shows an exploded view of a system for mixing at least two components with the opening device according to the first embodiment.

FIG. 6 shows a system for mixing two components. The structural parts of the opening device are depicted on the left-hand side of the figure. Identical structural parts have the same reference signs as in FIGS. 1 to 5. The right-hand side of the figure depicts a mixing container 18 with a connecting piece 19, which cooperates with the connecting piece 14 of the opening device in such a way that a fluid connection is established between the housing of the opening device and the interior of the mixing container 18. A mixing paddle 20 with a piston rod is provided at the end of the mixing container 18 remote from the connecting piece 19. The mixing paddle 20 protrudes into the interior of the mixing container 18 and is movable relative to the housing of the mixing container 18 by means of the piston rod. In order to dispense the mixture from the mixing container, the piston rod is broken off behind the mixing paddle. Using another applicator, force is then applied to a piston, which presses the mixture out of the mixing container.

In one embodiment, a bone cement in powder form is provided in the interior of the mixing container. A fluid monomer is accommodated in the ampule 3 of the opening device. To produce a bone cement, the mixing container 18 is fitted with the connecting piece 19 onto the connecting piece 14 of the opening device. The rotary drum 8 is then gripped by the handle 9 with one hand, and either the mixing container 18 or the housing 1 is gripped with the other hand. With this maneuver, the rotary drum 8 can be easily rotated through 90° inside the second housing chamber 2. The head part 6 of the ampule 3 is thus broken off by the pins 16, and the passage 10 comes to lie opposite the outlet 13. The monomer flows from the interior of the glass ampule 3 into the rotary drum 8 and from there through the filter 11 of the passage 10 and through the outlet 13 via the fluid connection of the connecting pieces 14 and 19 into the interior of the mixing container 18. As soon as the fluid has flown into the mixing container 18, the rotary drum 8 can be turned back such that the valve is closed. The monomer located in the mixing container 18 and the cement powder can now be mixed together in the interior of the mixing container by sliding the mixing paddle 20 in and out. The opening device can then be detached from the mixing container, and a dispensing needle can be fitted onto the connecting piece 19 of the mixing container 18. The bone cement has in the meantime assumed a consistency allowing it to be dispensed through the dispensing needle by means of a forward thrust of the applicator within the mixing container.

FIGS. 7 to 10 show a second advantageous embodiment of an opening device according to the present invention. In this embodiment, the second housing chamber 2 has, in the jacket wall or circumferential wall, another connector 21 to which a device for generating an underpressure in the housing of the opening device can be attached. The connector is designed as a channel stump such that, for example, a line of a pump can be fitted or screwed onto it. In the channel stump there is a nonreturn valve, which closes as soon as the underpressure device is detached or switched off. An underpresure is generated in the volumes of the individual chambers of the housing of the opening device and of the mixing system, depending on how the position of the rotary drum in the second housing chamber is chosen. The application of the underpressure can be controlled by the valve function of the rotary drum.

Figures 7A, 7B:
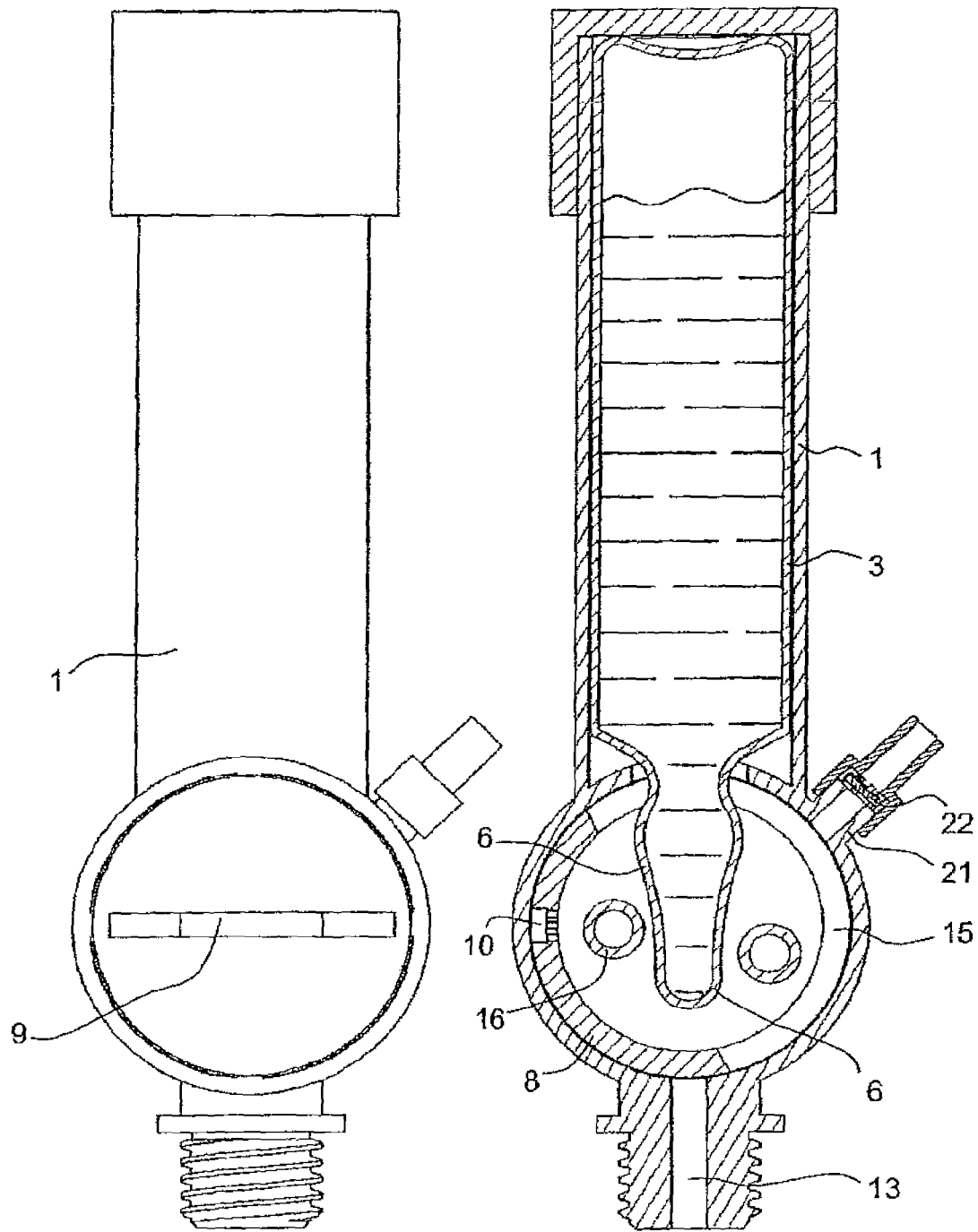
FIG. 7a shows a sectional view of an opening device according to a second embodiment, with a vacuum connector, in a closed position.
FIG. 7b shows a view according to FIG. 7a, seen from the outside.

In FIG. 7a, the opening device is shown in a position in which the rotary drum 8 covers the outlet 13. The valve is closed, which is also indicated by the transverse position of the handle 9 (see FIG. 7b). The connector 21 lies opposite the oblong hole 15 of the rotary drum 8. If an underpressure is now generated in the chambers of the housing of the opening device via the connector 21, no underpressure builds up in the mixing container of an attached mixing system or in other opening devices attached by way of the mixing container.

Figures 8A, 8B:
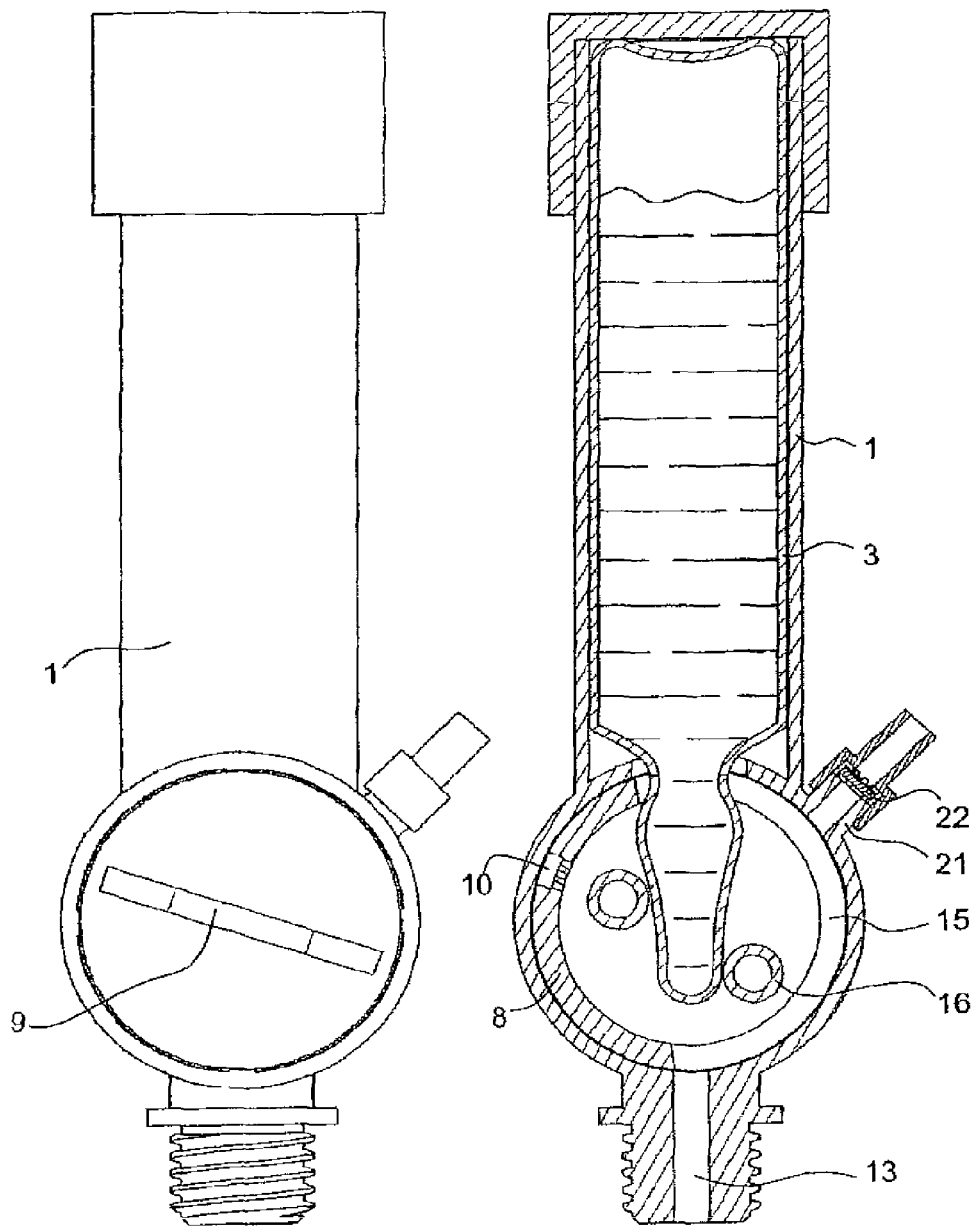
FIG. 8a shows a sectional view of the opening device from FIG. 7a in a position for generating an underpressure.
FIG. 8b shows a view according to FIG. 8a, seen from the outside.

FIG. 8a shows the rotary drum 8 in the second housing chamber 2 in an opened position in which the oblong hole 15 comes to lie opposite the outlet 13 and, therefore, the volumes of the housing of the opening device and of the mixing container of a mixing system are interconnected. The valve is thus opened, as can also be seen from the first oblique position of the handle 9 in FIG. 8b. In this embodiment, the two pins are arranged at such a distance from each other, next to the head part 6 of the ampule, that they have sufficient play to ensure that, upon slight rotation of the rotary drum from the starting position to the opened position, they do not yet separate the head part 6. If an underpressure is now applied to the second housing chamber 2 via the connector 21, an underpressure is generated in the entire system via the passage through the oblong hole 15 and the outlet 13, i.e. the opened valve function of the rotary drum.

Figure 9B:
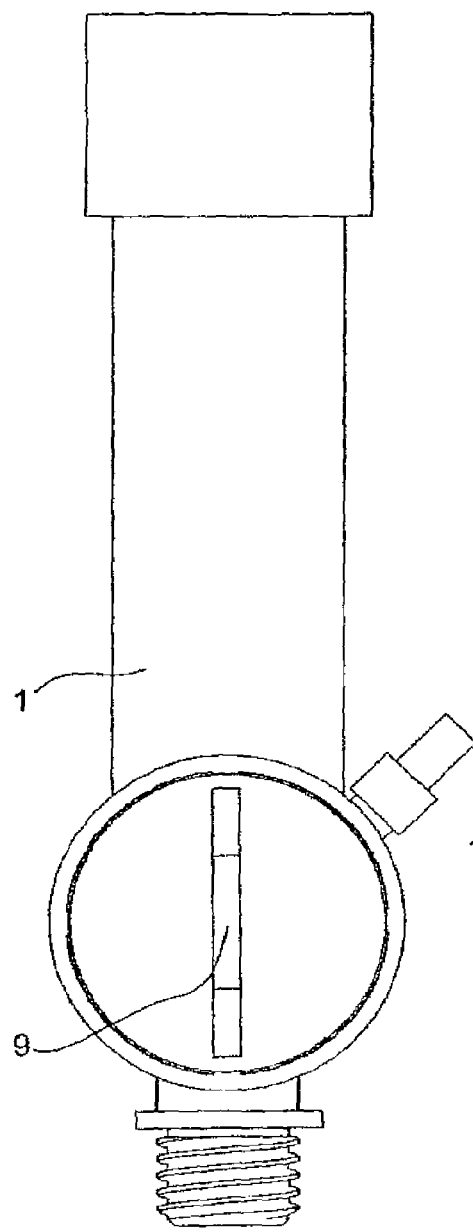
FIG. 9b shows a view according to FIG. 9a, seen from the outside.
Figure 9A:
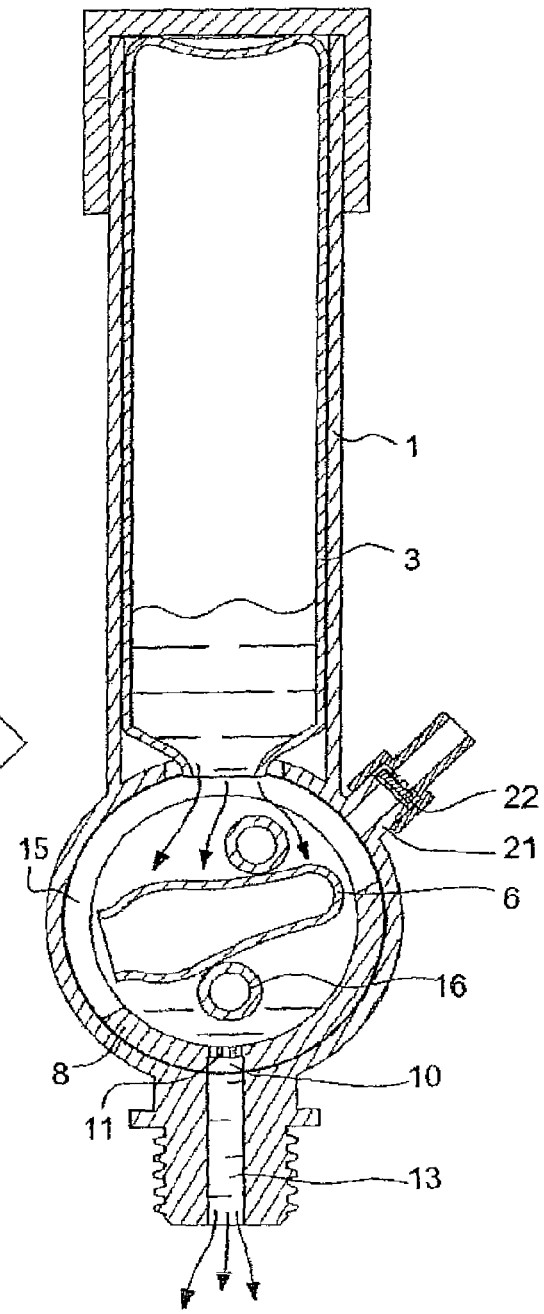
FIG. 9a shows a sectional view of the opening device from FIG. 7a in a separating position.

In FIG. 9a, the rotary drum 8 is located in a separating position in which, on the one hand, the head part 6 has been separated from the ampule 3 by means of the pins 16 and, on the other hand, the filter 11 comes to lie opposite the outlet 13. As soon as the head part 6 is separated, the content of the ampule is sucked or forced out of the latter, since there is a higher pressure in the interior of the ampule than in the volumes of the mixing system. The fluid is therefore reliably discharged completely from the ampule. In this position, the valve is likewise opened, as can be seen from the longitudinal position of the handle 9 in FIG. 9b, but the outlet 13 is covered by the filter 11.

Figures 10A, 10B:
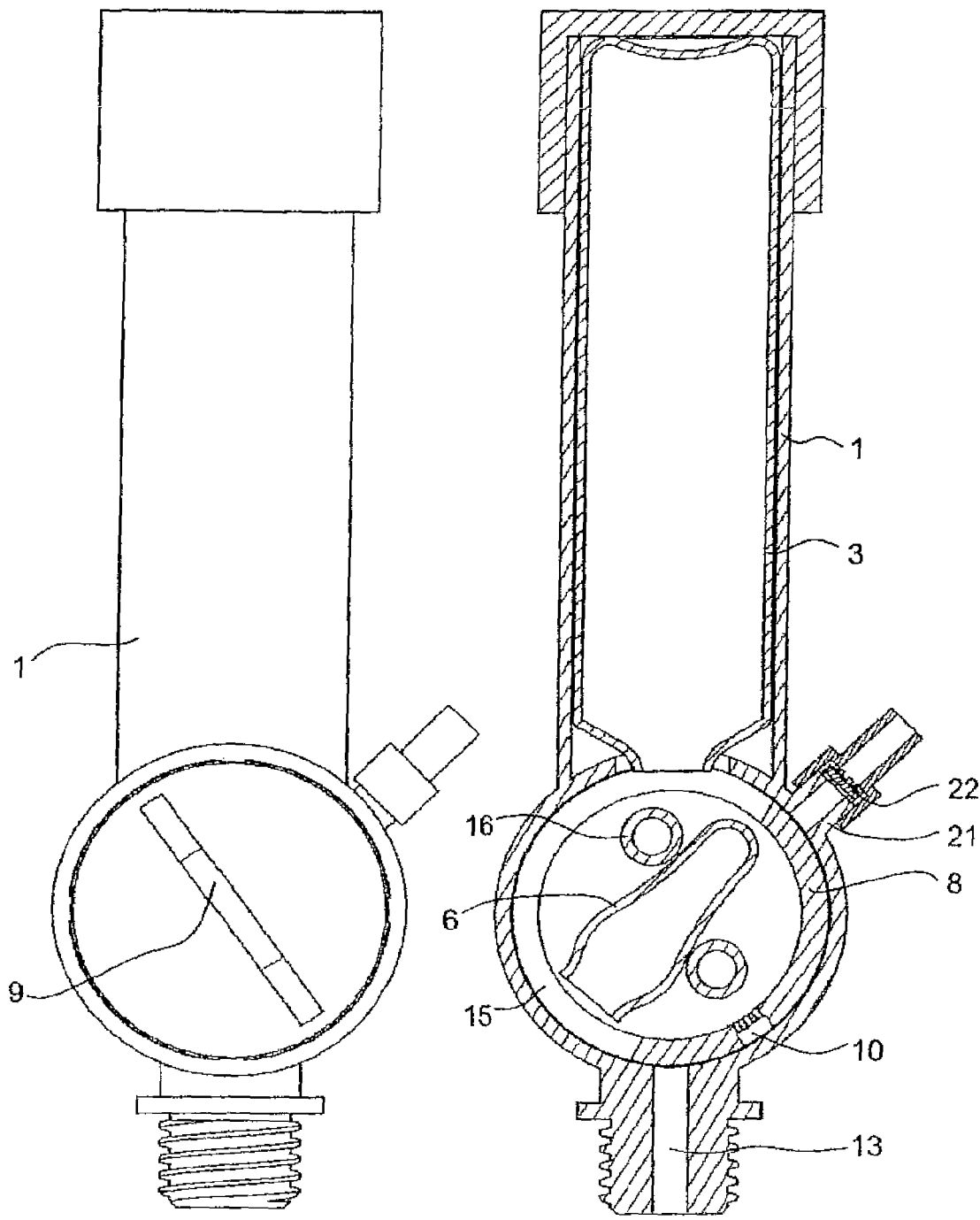
FIG. 10a shows a sectional view of the opening device from FIG. 7a after a part of the fluid container has been separated, with the valve closed.
FIG. 10b shows a view according to FIG. 10a, seen from the outside.

FIG. 10a shows the rotary drum 8 once again turned to a closed position in which the circumferential wall of the rotary drum covers and closes off the outlet 13.

This can be seen from the second oblique position of the handle 9, which is the opposite of the first oblique position (see FIG. 10b). The underpressure in the system is still maintained, since the nonreturn valve is closed and since there is still also the connection between the mixing container and the opening device. The circumferential wall of the rotary drum closes the underpressure connector in this position. In this state, the mixture can be mixed free from bubbles. The opening device can then be detached, or a dispensing needle need simply be fitted onto the mixing container.

On the outside of the housing of the opening device, a labeling can be provided for the individual positions of the handle 9 according to FIGS. 7b to 10b, with the aid of which labeling the position of the rotary drum, and therefore the state of the mixing system, can be read off easily.

Figure 11A:
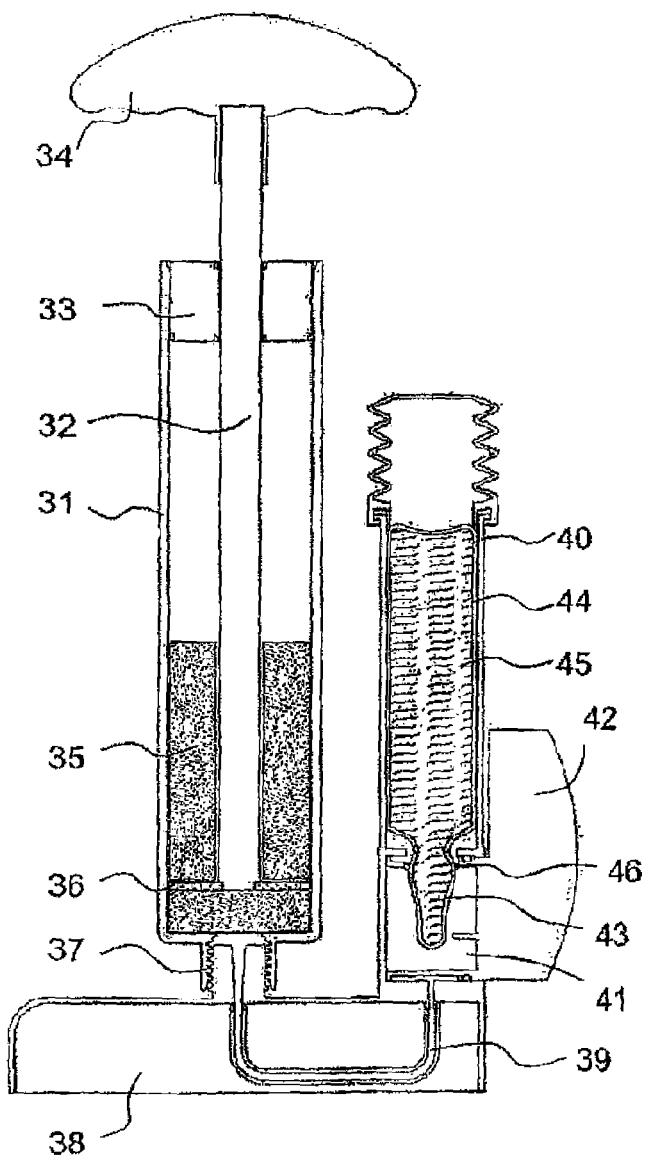
FIG. 11a shows a schematic sectional view of a system for mixing with an opening device according to a third embodiment, in a starting position.
Figure 11B:
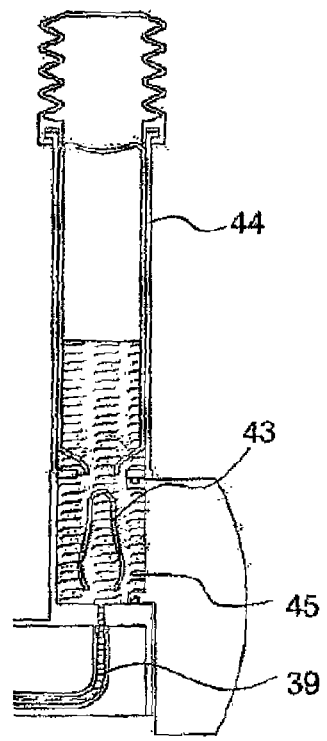
FIG. 11b shows a schematic sectional view of a part of the system from FIG. 11a in a separating position.

FIGS. 11a and 11b show a system for mixing two components using a third embodiment of an opening device according to the invention. The system comprises, on the one hand, a mixing device and, on the other hand, the associated opening device.

The mixing device has a mixing chamber 31 with a first component 35 received therein, for example a component in powder form. The mixing chamber is closed at its upper end by a stopper 33 in which a piston rod 32 is guided. A handle 34 is fitted on the upper end of the piston rod. A mixing element 36, which can have the form of a perforated plate for example, is secured on the other end of the piston rod 32 in the interior of the mixing chamber 31.

By way of an attachment 37, e.g. a bayonet or screw connection, the mixing device is connected releasably to a base part 38 in which a line 39 runs. The line 39 forms a fluid connection between the mixing device and the opening device. A filter can in each case be provided at one or both ends of the line 39 such that, on the one hand, the first component 35 is held back in the mixing chamber and, on the other hand, impurities or splinters, which can result from opening the ampule for example, are held back in the opening device. On the rear face of the mixing chamber 31, the upper part of the mixing chamber has a connector piece (not shown) for an underpressure device that can generate an underpressure in the mixing chamber.

The opening device is mounted on the base part 38. This opening device comprises a housing 40 into which an ampule 44 is inserted head 43 first from the top end. A second, liquid component 45 is present in the ampule 44. At the top end, the housing 40 is closed off by a bellows-like closure piece.

The ampule head 43 comes to lie in a rotary drum 41, which is arranged in a lower, drum-like housing area and which is only shown schematically here. The rotary drum 41 is sealed off from the housing 40 by an O-ring. The rotary drum 41 is rotatable in the housing 40 about a rotation axis arranged transversely with respect to the longitudinal axis of the ampule. It is provided with a handle 42 in the form of an upright plate, which protrudes laterally from the rotary drum 41 in the continuation of the rotation axis. The handle 42 is configured asymmetrically in relation to the rotation axis and protrudes with one end of the handle radially beyond the circumferential wall of the rotary drum. In the starting position in FIG. 11a, the protruding area of the handle is directed upward, away from the base part 38, and thus indicates that the rotary drum is located in the starting position, in which the ampule 44 is closed.

In FIG. 11b, the rotary drum has been turned through 180° to a separating position, in which the rotary drum has separated the ampule head 43 from the body of the ampule 44. The protruding area of the handle is now directed downward, in the direction of the base part 38, and indicates that the ampule has been opened. The protruding area allows the user to grip the handle securely. During rotation, the protruding area permits an increased lever action, such that opening is possible with relatively little force.

When the ampule 44 is opened, some of the component 45 accommodated therein flows into the line 39 and into the mixing chamber 31. In addition, the underpressure device is now activated, as a result of which an underpressure is generated in the mixing chamber 31. In this way, the rest of the second component 45 is conveyed through the line 39 into the mixing chamber 31. This empties the ampule 44 and also the ampule head 43, which is held by the rotary drum with the opening directed downward. The underpressure can be seen from the outside by virtue of the bellows contracting.

As soon as the second component 45 has been transferred into the mixing chamber 31, the piston rod 32 is gripped via a handle 34, and the mixing element 36 is moved by sliding the piston rod 32 in the mixing chamber 31 in and out and turning it, in order to mix the components with each other. For this purpose, the mixing device can be removed from the base unit 38 or can remain thereon.

In the illustrative embodiment shown, the opening device is connected fixedly to the base unit 38. Alternatively, however, it is also possible for the opening device to be connected releasably to the base unit.

LIST OF REFERENCE SIGNS 1 first housing chamber
2 second housing chamber
3 glass ampule
4 closure cap
5 opening
6 head part/glass ampule
7 shoulder
8 rotary drum
9 handle
10 passage
11 filter
12 sealing ring
13 outlet
14 connecting piece
15 oblong hole
16 pin
17 guide edge
18 mixing container
19 connecting piece
20 mixing paddle
21 underpressure connector
22 nonreturn valve

The invention claimed is:

1. A system for mixing at least two components, comprising:
   at least one opening device for opening a closed fluid container, the opening device comprising:
      a housing with a first chamber for receiving the fluid container and with a second chamber connected to the first chamber and having an outlet, the second chamber being adapted to receive a separable part of the fluid container, and
      a rotary drum guided rotatably in the second chamber about a rotation axis and having at least one separating element which, in a starting position, is offset in relation to the separable container part and, by a rotation of the rotary drum about the rotation axis, is adapted to be brought to a separating position, in which it separates the separable container part from the fluid container,
      the first and second chambers defining a connection axis, and the rotation axis of the rotary drum extending at an angle to this connection axis,
      the second chamber being shaped like a drum and having a jacket wall that extends in a circumferential direction about the rotation axis of the rotary drum, and the outlet of the second chamber being formed in the jacket wall of the second chamber; and a mixing container with at least one connecting piece to which the at least one opening device is removably connected in order to establish a fluid connection, and with a mixing device for mixing components in the mixing container.

2. The system as claimed in claim 1, wherein a connector for generating an underpressure in the system is present on the mixing container.

3. The system as claimed in claim 1, wherein the connecting piece of the mixing container is adapted for attachment of a dispensing nozzle or dispensing needle.

4. The system as claimed in claim 1, wherein the outlet of the second chamber is arranged along the connection axis and opposite the first chamber.

5. The system as claimed in claim 1, wherein the outlet of the second chamber opens into a connecting piece for releasable attachment to the mixing container.

6. The system as claimed in claim 1, wherein the rotary drum has a circumferential wall with at least one passage which, in the starting position, lies opposite the jacket wall of the second chamber, such that the circumferential wall of the rotary drum closes the outlet in the starting position, and which frees the outlet in a rotated position, as a result of which a valve function is obtained.

7. The system as claimed in claim 6, wherein the passage in the rotary drum has a filter.

8. The system as claimed in claim 1, wherein a guide is provided between the second chamber and the rotary drum, with a rotation limit stop in a first direction of rotation, such that a rotation is stopped in the separating position, and with a rotation limit stop in a second direction of rotation, such that a rotation is stopped in the starting position.

9. The system as claimed in claim 1, wherein the rotation axis of the rotary drum is substantially perpendicular to the connection axis between the first and second chambers.

10. The system as claimed in claim 1, wherein the rotary drum has a handle, which protrudes from the second chamber and is designed for rotating the rotary drum in the second chamber.

11. The system as claimed in claim 10, wherein the handle comprises a grip plate extending from the rotary drum.

12. The system as claimed in claim 10, wherein the handle is configured asymmetrically with respect to the rotation axis of the rotary drum.

13. The system as claimed in claim 1, wherein the housing has a connector for generating an underpressure in the housing.

14. The system as claimed in claim 1, wherein the at least one separating element is designed such that is holds the separable container part after the separation of the separable container part from the fluid container.

15. The system as claimed in claim 1, wherein the rotary drum has two separating elements, the two separating elements being arranged such that they act on the separable container part from two opposite sides of the container part.

16. The system as claimed in claim 1, wherein the at least one separating element extends from the bottom of the rotary drum and is arranged offset from the center point of the rotary drum.

* * * * *